United States Patent [19]

Rosencwaig et al.

[11] Patent Number: 4,632,561
[45] Date of Patent: Dec. 30, 1986

[54] EVALUATION OF SURFACE AND SUBSURFACE CHARACTERISTICS OF A SAMPLE

[75] Inventors: Allan Rosencwaig, Danville; Jon Opsal, Livermore, both of Calif.

[73] Assignee: Therma-Wave, Inc., Fremont, Calif.

[21] Appl. No.: 728,759

[22] Filed: Apr. 30, 1985

[51] Int. Cl.[4] ............................................. G01N 21/47
[52] U.S. Cl. .................................... 356/432; 356/446; 374/5; 374/57
[58] Field of Search ............... 356/376, 381, 432, 446; 374/5, 7, 57, 129, 130

[56] References Cited

U.S. PATENT DOCUMENTS

| | | | |
|---|---|---|---|
| 4,243,329 | 1/1981 | Frosch et al. | 374/43 X |
| 4,255,971 | 3/1981 | Rosencwaig | 356/432 T X |
| 4,284,356 | 8/1981 | Heitman | 356/445 X |
| 4,513,384 | 4/1985 | Rosencwaig | 73/606 X |
| 4,521,118 | 6/1985 | Rosencwaig | 356/376 X |
| 4,522,510 | 6/1985 | Rosencwaig et al. | 374/5 X |
| 4,579,463 | 4/1986 | Rosencwaig et al. | 374/57 |

Primary Examiner—Eugene R. LaRoche
Assistant Examiner—James C. Lee
Attorney, Agent, or Firm—Limbach, Limbach & Sutton

[57] ABSTRACT

A method and apparatus is disclosed for evaluating surface and subsurface features in a sample by detecting scattering of a probe beam. More particularly, the subject invention relates to the detection of thermal and/or plasma waves through the phenomenon of optical scattering. The apparatus includes a periodic excitation source for supplying energy to the surface of the sample to generate thermal and/or plasma waves. A radiation probe is directed to the surface of the sample within the area that is being periodically excited and in a manner that the probe beam is scattered from the excited area. Variations of the intensity of the scattered probe beam are detected and processed to evaluate surface and subsurface characteristics of the sample.

12 Claims, 1 Drawing Figure

EVALUATION OF SURFACE AND SUBSURFACE CHARACTERISTICS OF A SAMPLE

TECHNICAL FIELD

The subject invention relates to a new and improved method and apparatus for evaluating surface and subsurface features in a sample by detecting scattering of a probe beam. More particularly, the subject invention relates to the detection of thermal and/or plasma waves through the phenomenon of optical scattering. The apparatus includes a periodic excitation source for supplying energy to the surface of the sample to generate either thermal and/or plasma waves. A radiation probe is directed to the surface of the sample within the area that is being periodically excited and in a manner that the probe beam is scattered from the excited area. Variations of the intensity of the scattered probe beam are detected and processed to evaluate surface and subsurface characteristics of the sample.

BACKGROUND OF THE INVENTION

There has been considerable effort expended in developing tools for the nondestructive analysis of materials. In the past, many devices using electrical, optical and acoustic detection systems have been developed for evaluating various parameters in a sample.

More recently, a new approach has been developed wherein information is derived by detecting thermal waves which have been generated in a sample and interact with various thermal features in the sample. Such an approach is described in "Thermal Wave Imaging" by Allan Rosencwaig, *Science Magazine*, Volume 218, p. 223, 1982, incorporated here by reference.

In a thermal wave system, a beam of energy, usually a laser or an electron beam, is focused and scanned across the surface of the sample. The beam is intensity modulated at a frequency in the 10 Hz to 10 MHz range. As the beam scans across the sample, it is absorbed at or near the surface and a periodic heating results at the beam modulation frequency. This periodic heating is the source of thermal waves that propagate from the heated region. The thermal waves are diffusive waves similar to eddy current waves, evanescent waves and other critically damped phenomena that travel only one or two wavelengths before their intensity becomes negligibly small. Nevertheless, within their range, the thermal waves interact with thermal features in a manner that is mathematically equivalent to scattering and reflection processes of conventional propagating waves. Thus, any features on or beneath the surface of the sample that are within the range of these thermal waves and that possess thermal characteristics different from their surroundings will reflect and scatter the thermal waves and thus become visible.

By measuring the thermal waves in a sample, a variety of surface and subsurface features can be evaluated. For example, minor lattice disruptions which are generally not detectable with conventional optical and acoustic probes can be detected with a thermal wave analysis. Other thermal features, such as mechanical defects, cracks, voids and delaminations can be detected. Thermal wave imaging also offers the opportunity for nondestructive depth profiling and determination of thin film layer thicknesses.

A number of approaches have been suggested for detecting these thermal waves. The first approach included the measurement of acoustic wave carriers that are generated by the thermal waves. This approach was described in U.S. Pat. No. 4,255,971, issued Mar. 17, 1981, to Rosencwaig. The above described technique, while accurate, is a "contact" technique, which requires the connection of a piezoelectric transducer to the sample.

More recently, there has been developed a number of noncontact thermal wave measurement techniques. In one technique, a radiation probe is directed within the periodically excited area on the surface of the sample in a manner to be specularly reflected. This probe beam will undergo periodic angular displacements because of the periodic local angular changes in the surface conditions of the sample induced by the presence of the thermal waves. These periodic angular displacements can be detected, using a split or bicell photodetector. This approach is described in U.S. Ser. No. 401,511, filed July 26, 1982, and now U.S. Pat. No. 4,521,118. The preferred embodiment of this approach is described in U.S. Ser. No. 481,275, filed Apr. 1, 1983, and now U.S. Pat. No. 4,522,510. The latter patents are incorporated herein by reference.

Another noncontact technique has recently been developed which includes the detection of changes in the reflectivity of a probe beam. More specifically, the index of refraction of a sample will vary as the sample is periodically heated. Accordingly, if a probe beam is reflected off the surface of the sample, a reflected probe beam will vary in intensity in a manner corresponding to the changes in the index of refraction of the surface of the sample. Since the changing index of refraction is a function of the changes in the surface temperature induced by the thermal waves, by detecting changes in the intensity of the probe beam, the thermal waves can be detected. A device for detecting thermal waves based on the changes in optical reflectivity is described in copending application, U.S. Ser. No. 612,075, filed May 21, 1984, assigned to the same assignee as the subject invention and incorporated herein by reference.

Recently, devices similar to the ones disclosed above have also been used to generate and detect plasma waves in a semiconductor. More specifically, if an intensity modulated energy beam is focused on the surface of a semiconductor, an electron-hole plasma can be created. This plasma can exhibit wave-like characteristics, as described in "Thermal and Plasma Waves in Silicon" by Jon Opsal and Allan Rosencwaig.

As described therein, the plasma density at the surface of the sample will vary based on the sample characteristics. Furthermore, the variations in plasma density will affect the refractive index at the surface of the sample. The changing refractive index can be measured utilizing some of the noncontact techniques which have previously been successful in the measurement of thermal waves. More specifically, a radiation probe can be reflected off the surface of the sample and changes induced in the radiation probe by the plasma induced changes in the refractive index can be monitored to obtain information about surface and subsurface characteristics of the sample.

Plasma density analysis can be used to evaluate ion dopant characteristics and other features which vary across the sample and also as a function of depth beneath the sample surface. An apparatus for detecting plasma density variations is described in copending application, U.S. Ser. No. 707,485, filed March 1, 1985, assigned to the same assignee as the subject invention and incorporated herein by reference.

The measurement techniques described above are extremely sensitive and suitable for microscopic applications. In each case, changes in either the intensity or angle of reflection of a probe beam which has been "specularly reflected" are measured. Because specular reflection is relied upon, the incoming angle of the probe beam and the location of the detector to capture the reflected probe beam must be accurately controlled. Where the sample has considerably varying surface topology, maintaining accurate control of the detector position, so as to always capture the reflected beam, can be difficult. For example, where the sample is nonplanar, the orientation of the probe beam and detector must be continuously varied as the probe beam is scanned over the surface of the sample. In addition, samples having relatively rough surfaces will cause a large percentage of the beam to scatter, thereby reducing the percentage of the probe beam that will exhibit specular reflection.

Accordingly, it would be desirable to develop an alternate technique for detecting thermal and/or plasma waves which did not rely on specular reflection of a probe beam. Preferably, the alternate technique would also be of the noncontact variety to permit evaluation in a manufacturing situation.

Accordingly, it is an object of the subject invention to provide a new and improved apparatus for detecting thermal and/or plasma waves.

It is another object of the subject invention to provide a new and improved apparatus for evaluating surface and subsurface features in a sample.

It is a further object of the subject invention to provide a new and improved apparatus for measuring thermal and/or plasma waves by detecting the optical scattering of a probe beam.

It is still a further object of the subject invention to provide a new and improved apparatus for detecting thermal and/or plasma waves which can be utilized in situations where measurable specular reflection of a probe beam is difficult to obtain.

SUMMARY OF THE INVENTION

In accordance with these and many other objects, the subject invention provides for a new and improved method and apparatus for evaluating surface and subsurface conditions of a sample. The subject invention is particularly suited for detecting thermal and/or plasma waves in a sample.

The apparatus includes a periodic excitation source for supplying energy to the surface of the sample to generate thermal waves and/or plasma density variations. A radiation probe beam is provided which is directed to the surface of the sample within the area that it is being periodically excited by the energy source. A detector is provided for measuring intensity changes of the radiation probe due to optical scattering of the probe beam from the periodically excited region on the surface of the sample. Finally, a means is provided for processing the measured intensity changes to evaluate the sample. The processing means functions to isolate the intensity changes which are a function of the periodic excitation. The mode of processing will be dependent, in part, upon whether thermal and/or plasma waves are being detected.

The processing approach will also vary depending upon the type of information sought. Various processing approaches are set forth in the above-cited patent and patent applications. Additional information concerning details of a thermal wave analysis can also be found in U.S. Pat. No. 4,513,384, issued Apr. 23, 1985, to Rosencwaig, incorporated herein by reference. The latter patent sets forth how additional information about a sample can be derived by varying the modulation frequency of the excitation source and observing changes in the thermal waves. A similar type of analysis can be performed when observing plasma waves.

The subject invention is particularly suited for measurement situations where the surface of the sample is a highly scattering medium. For example, if the sample has a rough surface, it can be difficult to arrange optical components in a manner to obtain good measurements of a specularly reflected probe beam.

The subject technique is also suitable where the sample is non-planar such that it would be difficult to locate the optical components near the surface of the sample. As discussed above, as the probe beam is rastered over the surface of the sample, the location of the specularly reflected beam can vary. This effect is increased when the optics are moved farther from the surface of the sample. Where the optics must be moved away from the sample surface, it becomes increasingly difficult to obtain measurements of a specularly reflected probe beam. In contrast, the subject invention can be used without focusing and permits the placement of the detector a significant distance from the sample surface.

Further objects and advantages of the subject invention will be apparent from the following detailed description taken in conjunction with the drawings in which:

DETAILED DESCRIPTION OF THE PREFERRED EMBODIMENT

Figure 1:
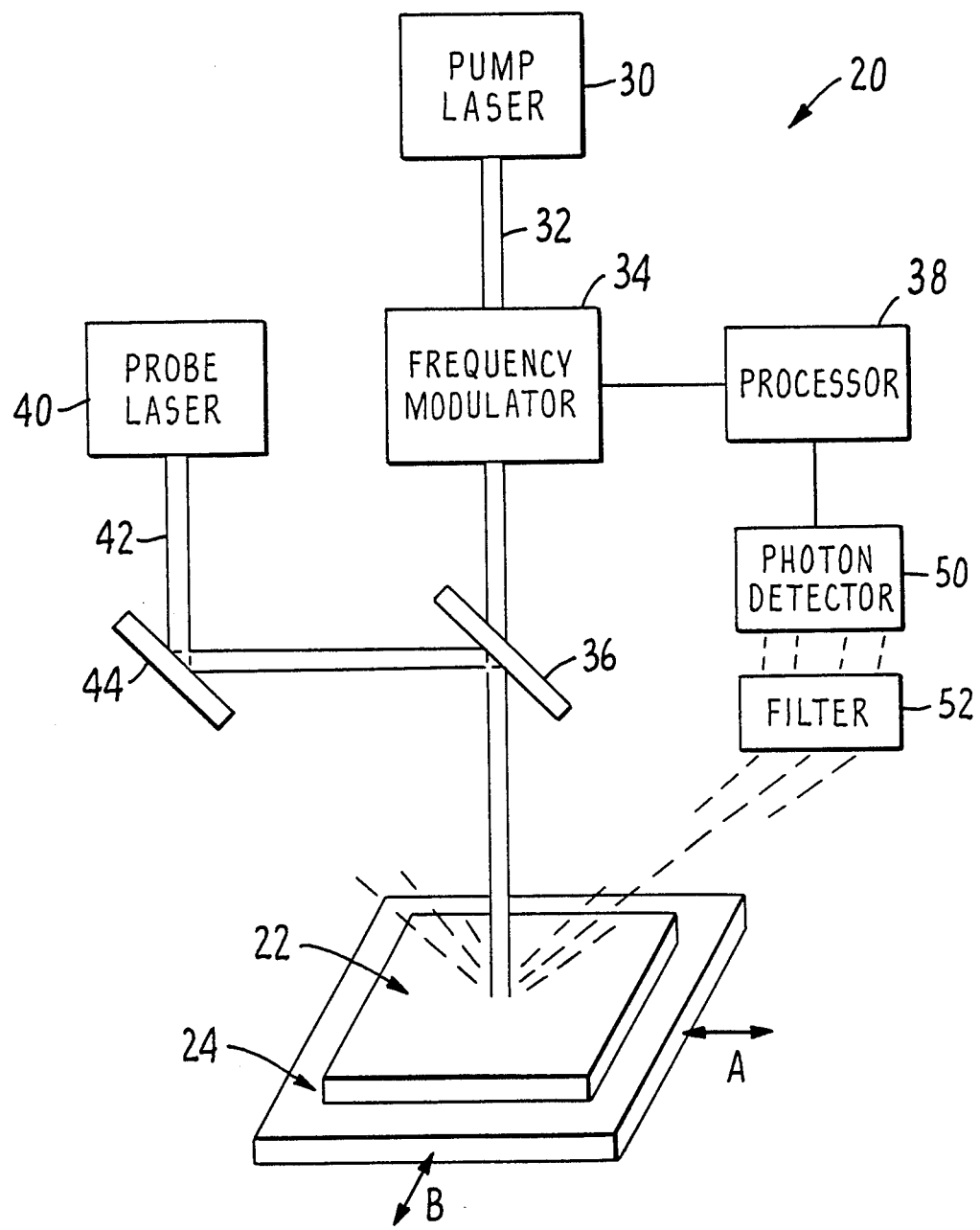
FIG. 1 is a schematic diagram of an apparatus for performing the method of the subject invention.

Referring to FIG. 1, there is illustrated an apparatus 20 for performing the method of the subject invention. As illustrated therein, a sample 22 is placed on a movable stage 24. The stage is capable of being rastered in two dimensions, as indicated by arrows A and B. Such movable stages are well-known in the prior art. It should be noted, however, that the sample could also be kept stationary, and the pump and probe beams scanned across the sample using appropriate optical deflection techniques.

In accordance with the subject invention, a means is provided for periodically exciting the sample. In the preferred embodiment, the means is provided by a laser 30. Laser 30 may be an argon-ion laser. The energy source or pump can also be provided from any suitable electromagnetic radiation or a particle beam, such as an electron beam. The energy of the beam must be sufficient to generate the thermal waves and/or plasma density variations of interest.

Laser 30 emits a beam 32 which is passed through a frequency modulator 34. The frequency modulator is intended to periodically chop or intensity modulate the beam at a frequency which is variable and under control of the processor 38. Beam 32 then passes through a dichroic mirror 36 to the surface of the sample. Dichroic mirror 36 is designed to pass the wavelengths of light emitted by the argon ion laser 30 and reflect the light of probe laser 40, as discussed below.

Beam 32 is directed to the surface of the sample in a manner to periodically excite the sample at its surface. In any sample, the periodic energy beam will function to create thermal waves having a frequency corresponding to the frequency of modulator 34. These thermal waves, while critically damped, will travel one to two wavelengths before becoming too weak to detect. The distance which the waves travel in the sample is given by the following equation:

$$u = (2K/\rho C\omega)^{\frac{1}{2}} \quad (1)$$

where u is the thermal diffusion length, K is the thermal conductivity, $\rho$ is the density, C is the specific heat, and $\omega$ is the modulation frequency of the beam.

Where a semiconductor material is being evaluated, the energy beam can produce an electron-hole plasma. An electron-hole plasma will be created if the energy of the beam is sufficient to raise electrons from the valence band to the conduction band, thereby creating electron hole pairs. Where the input energy exceeds the band gap energy, thermal waves may also be produced. In any event, when the energy exceeds the band gap energy, electrons which have been excited above the conduction band will, in a relatively short period of time (tau [$\tau$] is approximatley equal to $10^{-13}$ seconds) give up a portion of their energy to the lattice through non-radiative transitions to the unoccupied states near the bottom of the conduction band. After a much longer time ($\tau = 10^{-3}$ to $10^{-8}$ seconds) these carriers will give up the remainder of their energy to the lattice by recombining with the holes of the valence band. Prior to this recombination, there exists a plasma of electrons and holes whose spatial density is governed by diffusion in a manner analogous to the flow of heat from a thermal source.

Equations which set forth the diffusion length of the periodic plasma density variations are set forth below. More specifically, in a situation where the decay time tau ($\tau$) (the time it takes for the electron hole pairs to recombine) is relatively short compared to the modulation period $1/\omega$, where $\omega$ is the modulation frequency in radian/second (i.e., $\omega\tau$ is less than one) then the diffusion length of the plasma is given by the following equation:

$$u = (D\tau)^{\frac{1}{2}} \quad (2)$$

where D is the diffusivity of the plasma. Note that in this situation plasma waves will not be generated. However, changes in plasma density can still be detected and used to derive information about the sample.

Where the decay time ($\tau$) is long compared to the period of the modulation of the energy beam ($\omega\tau$ is greater than one) a plasma wave will be created and the diffusion length is given by the following equation:

$$u = (2D/\omega)^{\frac{1}{2}} \quad (3)$$

The above equations which define the diffusion lengths are provided in order to define the area of the sample which is being "periodically excited." More specifically, and as discussed below, in order to detect the thermal waves and/or plasma density variations, the beam 42 from probe laser 40 must be directed within the periodically excited area on the surface of the sample. This periodically excited area can be defined in terms of an excited diameter "D" by the following equation:

$$D = 2\sqrt{(\text{spot radius } R_o)^2 + (\text{diffusion length})^2} \quad (4)$$

where the spot radius $R_o$ is defined by the radius of the modulated energy beam. The second term of the equation, diffusion length, is given by one of the formulas (1-3) set forth above and will depend on the particular measurement situation. Specifically, where only thermal waves are being measured, the thermal diffusion length u is set forth in equation (1). Similarly, the plasma wave diffusion length equations can be substituted in the proper circumstances. If both thermal and plasma waves are present, the exicted area will be defined as the largest of the calculated regions.

Referring again to FIG. 1, it will be seen that the subject invention further includes a radiation probe 40 which can be defined by an optical beam. The radiation probe should emit a beam which is capable of optical scattering. In the preferred embodiment, probe 40 is defined by a helium-neon laser.

Beam 42 is deflected by a mirror 44 and onto dichroic mirror 36. The dichroic mirror is optically reflective to the wavelengths emitted by probe laser 40. As illustrated in FIG. 1, the probe laser beam is directed to be coincident with the pump laser beam 32. However, it is only necessary that the probe laser beam be directed within the periodically excited region which emanates from the modulated heating beam 32 and extends a distance as defined by equation (4). Note that where the diffusion length is very short, the periodically excited region will be essentially coincident with the periodic energy beam.

In most situations, the probe beam will be specularly reflected from the surface of the sample. In addition, portions of the beam will also be scattered. Scattering of a probe beam will generally take place whether or not the energy beam is impinged on the sample. Thus, there will generally be a constant or DC scattering signal which is dependent upon the strength of the probe laser and on the local scattering characteristics of the sample surface. As discussed below, when a periodic excitation source 30 is directed on the surface of the sample, a periodic scattering phenomenon will also occur that is a function of the thermal waves and/or plasma density variations on the surface of the sample.

The scattering of the probe beam may be detected by a photon detector 50. The photon detector 50 can be, for example, a photodetector or photomultiplier tube. Preferably, a filter 52 is provided in front of the input of the detector 50 which allows optical energy from the probe laser to pass, but shields the detector from any radiation from the pump laser beam 32. As can be appreciated, a detector 50 which is adapted to detect impacting photons, will measure both the "DC" scattering and the periodic scattering induced by the presence of thermal and/or plasma waves.

The reason that the scattering is affected by the presence of the thermal and/or plasma waves relates to the fact that the optical properties of the sample are being periodically modulated. For example, in the case of a modulation in the index of refraction, this dependence can be expressed by the following equations:

$$S = S_o + \Delta S \quad (5)$$

where S is the total scattering and $S_o$ is the DC scattering. The term $\Delta S$ is defined in equation (6).

$$\Delta S = (dS/dn)\Delta n \quad (6)$$

where $\Delta S$ is the change in optical scattering and $\Delta n$ is the change in the complex refractive index which may represent changes induced by either the thermal or plasma waves. From the above equations, it can be seen that the total scattering can be defined as follows:

$$S = S_o[1 + 1/S_o(dS/dn)\Delta n] \quad (7)$$

The term $1/S_o (dS/dn)$ represents the complex refractive coefficient for scattering.

Thermal waves can also affect the local geometry of the sample surface. Specifically, the roughness of the surface that produces the DC scattering may also be modulated to some extent by the local thermoelastic expansion of the sample from the thermal waves. This geometric modulation of the sample surface roughness may also contribute to the AC scattering signal. Such an effect has not been observed with plasma waves.

Where DC scattering is present, the output signal generated by detector 50 will include both this DC scattering and the frequency dependent variations in intensity. As the sample is translated past the pump and probe beams, the amount of DC scatterin $S_o$, into the photon detector, will vary as the local DC scattering characteristics vary. Thus, as seen in equation (7), for a fixed refractive coefficient of scattering $1/S_o(dS/dn)$, the AC signal will also vary as $S_o$.

In order to derive the variations in intensity which are purely a result of the thermal or plasma wave induced modulation of the scattering, the signal is normalized. More specifically, the signal of interest is examined by normalizing out any output signals from the detector which are not synchronous with the excitation modulation frequency or any of its harmonics. One method of deriving the desired signals is to divide the DC signal into the detected signal. The normalized output gives a measure of the thermal or plasma wave activity in a sample.

The normalized output signal can then be analyzed in a manner described in any of the above patents or applications to derive information about the sample. For example, the signal may be compared to a previously recorded signal of a known sample. Variations between the predetermined signal and the measured signal will indicate variations in the composition of the material. Where dopant concentrations are to be measured, variations in the signal as the probe and energy beam are scanned across the sample surface will give a measure of the varying dopant concentrations mapped out in a two-dimensional image.

The above described measurements assume that there would be some steady state or DC scattering $S_o$. However, in some situations, there may be little or no steady state optical scattering. For example, where a sample surface is highly polished, virtually all of the probe beam energy will be "specularly" reflected rather than scattered. In such a case, it may be difficult to obtain measurements of thermal wave and/or plasma wave induced scattered light. However, the subject method should still prove feasible provided that focused laser beams are utilized. More specifically, if the probe and pump lasers are focused down to approximately the wavelength of light, measurable thermal wave and/or plasma wave induced scattering will be present since now the geometry of the scatterer, which in this case is the thermal and/or plasma wave itself, approaches the wavelength of the probe beam. This also necessitates the use of high modulation frequencies to generate shortwave length thermal and/or plasma waves.

In order to focus the beams, it would then be necessary to provide a lens system (not shown) between the mirror 36 and the sample 22. Of course, such focusing would be needed even in the more usual case of samples with DC scattering, if investigations of surface and subsurface features need to be performed on a microscopic scale.

As can be appreciated, in the above described limiting case (where little or no steady state scattering is present), it would be necessary to have the optics and detector fairly close to the sample. Since most samples will produce steady state scattering, there would be no need for the close alignment that is required in other optical techniques for detecting thermal and/or plasma waves. For the latter reason, the subject invention is quite desirable in manufacturing situations. Furthermore, it is also desirable for macroscopic type examinations and for samples having irregular shapes.

In summary, there has been provided a new and improved apparatus for evaluating surface and subsurface features in a sample. The apparatus includes a periodic excitation source for generating thermal and/or plasma waves in a sample. A radiation probe is directed to the surface of the sample within the area which has been periodically excited. A means is provided for measuring a portion of the probe beam which has been optically scattered. Finally, a means is provided for processing the output signals corresponding to the intensity changes of the scattered probe beam that are a function of the periodic variations.

While the subject invention has been described with reference to a preferred embodiment, it is to be understood that various changes and modifications could be made therein by one skilled in the art without varying from the scope and spirit of the subject invention as defined by the appended claims.

We claim:

1. An apparatus for evaluating surface and subsurface features in a sample comprising:
   a periodic excitation source for supplying energy to the surface of the sample;
   a radiation probe beam;
   means for directing said probe beam within at least a portion of the area on the surface of the sample which is being periodically excited such that a portion of said probe beam is scattered from the periodically excited area;
   means for monitoring intensity changes of the scattered probe beam radiation and generating an output signal corresponding thereto; and
   means for processing the output signal corresponding to the measured intensity changes of the scattered probe beam to evaluate the sample.

2. An apparatus as recited in claim 1, wherein the processing means normalizes the output signal from the monitoring means to derive intensity changes that are a function of the periodic excitation source.

3. An apparatus as recited in claim 2 wherein said processing means derives the intensity changes that are a function of the periodic excitation source by normalizing out any output signal that is not synchronous with the excitation modulation frequency or any of its harmonics.

4. An apparatus as recited in claim 1 wherein said periodic excitation source is an optical beam.

5. An apparatus as recited in claim 1 wherein said periodic excitation source is defined by an intensity modulated laser beam.

6. An apparatus as recited in claim 1 wherein said radiation probe beam is an optical beam.

7. An apparatus as recited in claim 1 wherein said radiation probe beam is defined by a laser beam.

8. An apparatus as recited in claim 1 wherein said monitoring means is defined by a photodetector.

9. An apparatus as recited in claim 1 wherein said monitoring means is a photomultiplier tube.

10. A method for evaluating surface and subsurface features in a sample comprising
    supplying periodic energy to the surface of the sample;
    directing a radiation probe onto at least a portion of the area on the surface of the sample which is being periodically excited, such that a portion of the probe beam is scattered from the periodically excited area;
    monitoring intensity changes of the scattered probe beam radiation;
    generating an output signal corresponding to the measured intensity changes; and
    processing the output signal corresponding to the measured intensity changes of the scattered probe beam to evaluate the sample.

11. A method as recited in claim 10 wherein said processing step includes normalizing the output signal to derive intensity changes that are a function of the periodic excitation source.

12. A method as recited in claim 10 wherein the processing step includes normalizing out any output signal measured that is not synchronous with the excitation modulation frequency or any of its harmonics.

* * * * *

Disclaimer

4,632,561—Allan Rosencwaig, Danville; Jon Opsal, Livermore, both of Calif. EVALUATION OF SURFACE AND SUBSURFACE CHARACTERISTICS OF A SAMPLE. Patent dated Dec. 30, 1986. Disclaimer filed Sept. 30, 1997, by the assignee, Therma-Wave, Inc.

The term of this patent shall not extend beyond the expiration date of Pat. No. 4,579,463.
*(Official Gazette, January 13, 1998)*